(12) United States Patent
Elli et al.

(10) Patent No.: US 12,740,583 B2
(45) **Date of Patent: *Sep. 22, 2026**

(54) SYNERGISTIC BLENDS OF PROBIOTICS EXPRESSING IMPROVED BENEFICIAL ACTIVITY FOR HUMAN HOST FAVOURABLY INTERACTING WITH FOOD, PARTICULARLY BABY FOOD

(71) Applicant: COREE S.R.L., Milan (IT)

(72) Inventors: Marina Elli, Milan (IT); Chong-Yoon Lim, Milan (IT)

(73) Assignee: COREE S.R.L., Milan (IT)

( * ) Notice: Subject to any disclaimer, the term of this patent is extended or adjusted under 35 U.S.C. 154(b) by 566 days.

This patent is subject to a terminal disclaimer.

(21) Appl. No.: 17/775,416

(22) PCT Filed: Nov. 11, 2020

(86) PCT No.: PCT/EP2020/081683

§ 371 (c)(1),
(2) Date: May 9, 2022

(87) PCT Pub. No.: WO2021/094336

PCT Pub. Date: May 20, 2021

(65) Prior Publication Data

US 2022/0395011 A1 Dec. 15, 2022

(30) Foreign Application Priority Data

Nov. 11, 2019 (EP) .................................... 19208263

(51) Int. Cl.
*A23L 33/00* (2016.01)
*A23L 33/135* (2016.01)
(Continued)

(52) U.S. Cl.
CPC ............ *A23L 33/40* (2016.08); *A23L 33/135* (2016.08); *A61K 35/745* (2013.01);
(Continued)

(58) Field of Classification Search
CPC .............. A61K 35/745; A61K 35/747; A61K 39/0011; A23V 2400/145;
(Continued)

(56) References Cited

U.S. PATENT DOCUMENTS 12,075,808 B2 * 9/2024 Elli ...................... A61K 36/899
2009/0304655 A1 12/2009 Donnet-Hughes et al.
2012/0076829 A1 * 3/2012 Vieites Fernandez .... A61P 1/00 424/282.1

FOREIGN PATENT DOCUMENTS

CN 107788317 A * 3/2018 ........... A23L 33/125
EP 2848681 A1 3/2015
(Continued)

OTHER PUBLICATIONS

U. G. A Nutraceuticals “RestoraFlor™ baby” First Date Available Feb. 15, 2022, on Amazon Italy. As obtained online. Retrieved from the internet: <URL:https://www.uganutraceuticals.com/product/restoraflor-baby>.*

(Continued)

*Primary Examiner* — Samira J Jean-Louis
*Assistant Examiner* — Amelia Nicole Dickens
(74) *Attorney, Agent, or Firm* — Bridgeway IP Law Group, PLLC; Sang Ho Lee; Hyun Woo Shin

(57) ABSTRACT

A probiotic food supplement includes a blend of strains of lactobacilli and bifidobacteria synergistically interacting with food (for instance milk), assuring thereby an improved beneficial effect on human health, especially 0-6 months babies, weaning babies, breastfed and formula fed infants as well as lactating mothers. Synergistic, i.e., synteractive
(Continued)

blends, have been designed to maximize their probiotic action when assumed with milk and/or food, in whatever state or formulation.

3 Claims, 3 Drawing Sheets

(51) Int. Cl.
*A61K 35/00* (2006.01)
*A61K 35/745* (2015.01)
*A61K 35/747* (2015.01)
*C12N 1/20* (2026.01)

(52) U.S. Cl.
CPC .............. *A61K 35/747* (2013.01); *C12N 1/20* (2013.01); *A23V 2002/00* (2013.01); *A23V 2200/3204* (2013.01); *A23V 2400/145* (2023.08); *A23V 2400/175* (2023.08); *A23V 2400/519* (2023.08); *A61K 2035/115* (2013.01)

(58) Field of Classification Search
CPC ........ A23V 2400/175; A23V 2400/775; A23V 2400/519; A23V 2400/531; A23L 33/40; A23L 33/135
See application file for complete search history.

(56) References Cited

FOREIGN PATENT DOCUMENTS

| | | | |
|---|---|---|---|
| KR | 10-1708871 | B1 | 2/2017 |
| WO | 2015/172191 | A1 | 11/2015 |

OTHER PUBLICATIONS

Dekker et al. "Safety aspects of probiotic bacterial strains *Lactobacillus rhamnosus* HN001 and *Bifidobacterium animalis* subsp. lactis HNO19 in human infants aged 0-2 years", 2008, International Dairy Journal, vol. 19, p. 149-154. (Year: 2008).*
English machine translation of CN-107788317-A (Year: 2018).*
Feleszko et al. "Probiotic-induced suppression of allergic sensitization and airway inflammation is associated with an increase of T regulatory-dependent mechanisms in a murine model of asthma", 2006, Clinical and Experimental Allergy, vol. 37, p. 498-505. (Year: 2006).*
Sagar et al. "*Bifidobacterium breve* and *Lactobacillus rhamnosus* treatment is as effective as budesonide at reducing inflammation in a murine model for chronic asthma", 2014, Respiratory Research, vol. 15, Article 46, p. 1-17. (Year: 2014).*
Shing et al. "Effects of probiotics supplementation on gastrointestinal permeability, inflammation and exercise performance in the heat", Oct. 23, 2013, European Journal of Applied Physiology, vol. 114, pp. 93-103 (Year: 2013).*
Zhang et al. "Isolation and Characterization of New Probiotic Strains From Chinese Babies", first available Sep. 10-12, 2017, copyright Nov./Dec. 2018, Journal of Clinical Gastroenterology, vol. 52, Supp. 1, p. S27-S34. (Year: 2017).*
Barbian, Maria E et al: "To start or not: Factors to consider when implementing routine probiotic use in the NICU". Early Human Development, Shannon, IR, vol. 135, Jun. 10, 2019 (Jun. 10, 2019), pp. 66-71, XP085743265, ISSN: 0378-3782, DOI: 10.1016/J.EARLHUMDEV.2019.05.009.
Kazemi, Asma et al: "Effect of probiotic and synbiotic supplementation on inflammatory markers in health and disease status: A systematic review and meta-analysis of clinical trials", Clinical Nutrition, Churchill Livingstone, London, GB, vol. 39, No. 3, Apr. 17, 2019 (Apr. 17, 2019), pp. 789-819, XP086055095, ISSN: 0261-5614, DOI: 10.1016/J.CLNU.2019.04.004.
Probiotical: "Our Probiotic Strains", , Jan. 1, 2016 (Jan. 1, 2016), XP055382106, Retrieved from the Internet: URL:http://bart.pl/wp-content/uploads/2016/11 /ceppi_2016_OK.pdf.
Luis Fontana et al: "Sources, isolation, characterisation and evaluation of probiotics", British Journal of Nutrition, vol. 109, No. S2, Jan. 1, 2013 (Jan. 1, 2013), pp. S35-S50, XP05530757 4, UK ISSN: 0007-1145, DOI: 10.1017/S0007114512004011.
Popova Metal: "Beneficial effects of probiotics in upper respiratory tract infections and their mechanical actions to antagonize pathogens", Journal of Applied Microbiology, Wiley-Blackwell Publishing Ltd, GB vol. 113, No. 6 Dec. 1, 2012 (Dec. 1, 2012), pp. 1305-1318, XP002711684, ISSN: 1364-5072, DOI: 10.1111 /J.1365-2672.2012.05394.X Retrieved from the Internet: URL:http://onlinelibrary.wiley.com/doi/10.1111 /.1365-2672.2012.05394.x/ abstract.
Deepika, G., Karunakaran, E., Hurley, C. R., Biggs, C. A. & Charalampopoulos, D. "Influence of fermentation conditions on the surface properties and adhesion of *Lactobacillus rhamnosus* GG". Microb. Cell Fact. (2012). doi:10.1186/1475-2859-11-116.
Dekker, J.W., Wickens, K., Black, P.N., Stanley ,T.V,Mitchell ,E.A., Fitzharris, P., Tannock,G.W., Purdie,G. and J. Crane (2009). "Safety aspects of probiotic bacterial strains *Lactobacillus rhamnosus* HN001 and *Bifidobacterium animalis* subsp. lactis HNO19 in human infants aged 0-2 years". International Dairy Journal 19, 149-154.
Duary, R. K., Rajput, Y. S., Batish, V. K. & Grover, S. "Assessing the adhesion of putative indigenous probiotic lactobacilli to human colonic epithelial cells". Indian J. Med. Res. 134, pp. 664-671 (Nov. 2011). doi:10.4103/0971-5916.90992.
El-Abasy, A. E., Abou-Gharbia, A., H., Mousa, H. M. & Youssef, M. M. "Mixes of Carrot Juice and Some Fermented Dairy Products: Potentiality as Novel Functional Beverages". Food Nutr. Sci., 2012, 3, 233-239. doi: 10.4236/fns.2012.32034.
Johansson, M. L. et al. "Administration of different *Lactobacillus* strains in fermented oatmeal soup: In vivo colonization of human intestinal mucosa and effect on the indigenous flora". Appl. Environ. Microbiol. 59, 15-20 (1993).
Joint FAO/WHO Working Group Report. "Probiotics in food—Health and nutritional properties and guidelines for evaluation" FAO Food and Nutrition Paper 85. Oct. 1, 2001.
Marshall E. & Mejia D. "Traditional fermented food and beverages for improved livelihoods—FAO Diversification booklet n. 21". (2011).
Tamang JP, Watanabe K, Holzapfel WH. "Review: Diversity of Microorganisms in Global Fermented Foods and Beverages". Front Microbiol. 2016;7:377. Published Mar. 24, 2016. doi:10.3389/fmicb.2016.00377.
Zhou, J.S., & Gill, H.S. (2005b). "Immunostimulatory probiotic *Lactobacillus rhamnosus* HN001 and *Bifidobacterium lactis* HN019 do not induce pathological inflammation in mouse model of experimental auto-immune thyroidites". International Journal of Food Microbiology; 103:97-104 (2005).
Zhou, U.S., Gopal, P.K., Prasad, J.,& Gill, H.S. (2000). "Potential probiotic lactic acid bacteria *Lactobacillus rhamnosus* (HN001), *Lactobacillus acidophilus*(HN017) and *Bifidobacterium lactis* (HN019) do not degrade gastric mucin in vitro". International Journal of Food Microbiology; 63:81-90 (2001).
Zhou, J.S., Rutherford, K.J., & Gill, H.S. (2005a). "Inability of probiotic bacterial strains *Lactobacillus rhamnosus* HN001 and *Bifidobacterium lactis* HNO19 to induce human platelet aggregation in vitro". Journal of Food Protection 68 (11); 2459-2464 (2005).

* cited by examiner

SYNERGISTIC BLENDS OF PROBIOTICS EXPRESSING IMPROVED BENEFICIAL ACTIVITY FOR HUMAN HOST FAVOURABLY INTERACTING WITH FOOD, PARTICULARLY BABY FOOD

The invention refers to a probiotic food supplement comprising a blend of strains of lactobacilli and bifidobacteria synergistically interacting with food (for instance milk) assuring thereby an improved beneficial effect on human health, with special reference to 0-6 months babies, weaning babies, breastfed and formula fed infants as well as lactating mothers.

Synergistic blends have been designed to maximise their probiotic action when assumed with milk and/or food, in whatever state or formulation.

BACKGROUND OF THE INVENTION

Probiotics are living microorganisms that, when administered in adequate amount, are able to exert beneficial effect on the host (FAO, 2002). Microbial strains with proven beneficial properties are available for human consumption as food (e.g. fermented milk) as well as food supplements and even drugs. The main and necessary feature to exert their beneficial action is that they have to be consumed in viable form and maintain their viability through the passage in the gut. The use of viable probiotics in some critical conditions appears to be questionable in expert's opinion.

Based on the current scientific literature probiotics express different cellular features when grown in different culturing media, due to the presence or lack of some nutrients and the subsequent activation or non-activation of some metabolic pathways. Very few reports considered the role of food as substrate for the growth of bacteria, with main reference to local traditional fermented food and no reports were found about the impact of the type of food in which the probiotic is grown on the human health status (Marshall & Mejia 2012; Tamang et al. 2016).

The scientific literature documented the role of mixtures of beneficial bacteria able to express stronger efficacy on human health than single strains. On the other hand, controversial reports are available about the fact that the synergistic action between strains in the mixtures needs to be demonstrated and ascertained in a reliable manner. In this case strains are usually tested following growth on laboratory media. Nobody considered the strong relevance of selecting beneficial strains able to express their maximal health effect in food and not only in laboratory media, in order to maximize their nutritive and beneficial value. This would represent a very precious tool to integrate with beneficial natural ingredients the diet of special category of consumers with very restricted food choice, such as weaning babies and elderly people.

The scientific community has reported several studies that support the efficacy of the multistrain mix composed of *L. rhamnosus* HN001 and *B. animalis lactis* HN019, especially in term of prevention of infections and pathologies in the respiratory tract in newborns (Dekker et al. 2009), in preservation of gut mucus layer (Zhou et al. 2000), in adhering to enterocytes and mucus-secreting cells present on the intestinal tract (Zhou et al. 2005) as well as having immunostimulatory properties are safe for the human health: in vivo studies have shown that taking the two strains does not induce autoimmune diseases, such as thyroiditis (Zhou & Gill, 2005). Nevertheless, nobody has focused on the possible antagonistic activity between mixed strains.

DESCRIPTION OF THE INVENTION

New probiotic strains were found to perform significantly better on food than traditional strains and to express a higher potential of interaction with human cell lines cultured in-vitro (e.g. higher adhesion to human mucosa and therefore higher colonization ability) (Duary et al. 2011).

The selected strains are therefore designed to be assumed by human consumers together with specific food in which they can express their beneficial potential at higher level (Deepika et al. 2012; El-Abasy et al. 2012; Johansson et al. 1993).

In particular, selected blends of lactobacilli and bifidobacteria were designed to better survive gastric and gut transit and to show an enhanced colonization ability, when co-administered with some food and food ingredients. The probiotic blends of the invention consist of strains of *Lactobacillus rhamnosus, Bifidobacterium breve* and a third strain selected from *Bifidobacterium animalis* subsp. *Lactis* or *Lactobacillus gasseri.*

According to a first embodiment, the invention provides probiotic food supplement comprising a probiotic blend, wherein the probiotic blend consists of strains of *Lactobacillus rhamnosus, Bifidobacterium breve* and a third strain selected from *Bifidobacterium animalis* subsp. *lactis* or *Lactobacillus gasseri.*

Strains of the above species are available in the market from several sources. *Bifidobacterium breve* M16V, available form Morinaga Milk Industries, is a preferred strain for use according to the invention. Said strain is available at the BCCM/LMG collection under the accession number LMG 23729.

According to a second embodiment, the invention provides the following new strains, deposited on 20 Nov. 2018 according to the Budapest Treaty at the BCCM/LMG collection (Ghent university, Belgium):

*Lactobacillus gasseri* LMG P-30998;

*Lactobacillus rhamnosus* LMG P-31000;

*Bifidobacterium breve* LMG P-30999.

A first preferred probiotic blend consists of *Bifidobacterium breve* M16V, *Lactobacillus rhamnosus* HN001 and *Bifidobacterium animalis lactis* HN019.

A further preferred probiotic blend consists of *Lactobacillus gasseri* LMG P-30998, *Lactobacillus rhamnosus* LMG P-31000 and *Bifidobacterium breve* LMG P-30999.

The beneficial advantage offered by the blends of the invention compared to single probiotic strains (monostrain formulation) has been shown in-vitro experiments. In particular, the advantage consists in the improved ability of the blends to interact with food, to survive gastric and intestinal transit and to adhere to gut mucosa and therefore to persist in the gut of the consumer as well as to displace gut pathogens.

The food supplement of the invention exhibits improved beneficial properties by synergistically interacting with the food. The probiotic blends provide in fact synergistic properties and favourably interact with the food to provide an effect which could be defined as "synteractive".

The probiotic food supplement of the invention is useful in the prevention of infections and pathologies in the respiratory tract in newborns, in preservation of gut mucus layer, in adhering to enterocytes and mucus-secreting cells present on the intestinal tract.

DETAILED DESCRIPTION OF THE INVENTION

Figure 1:
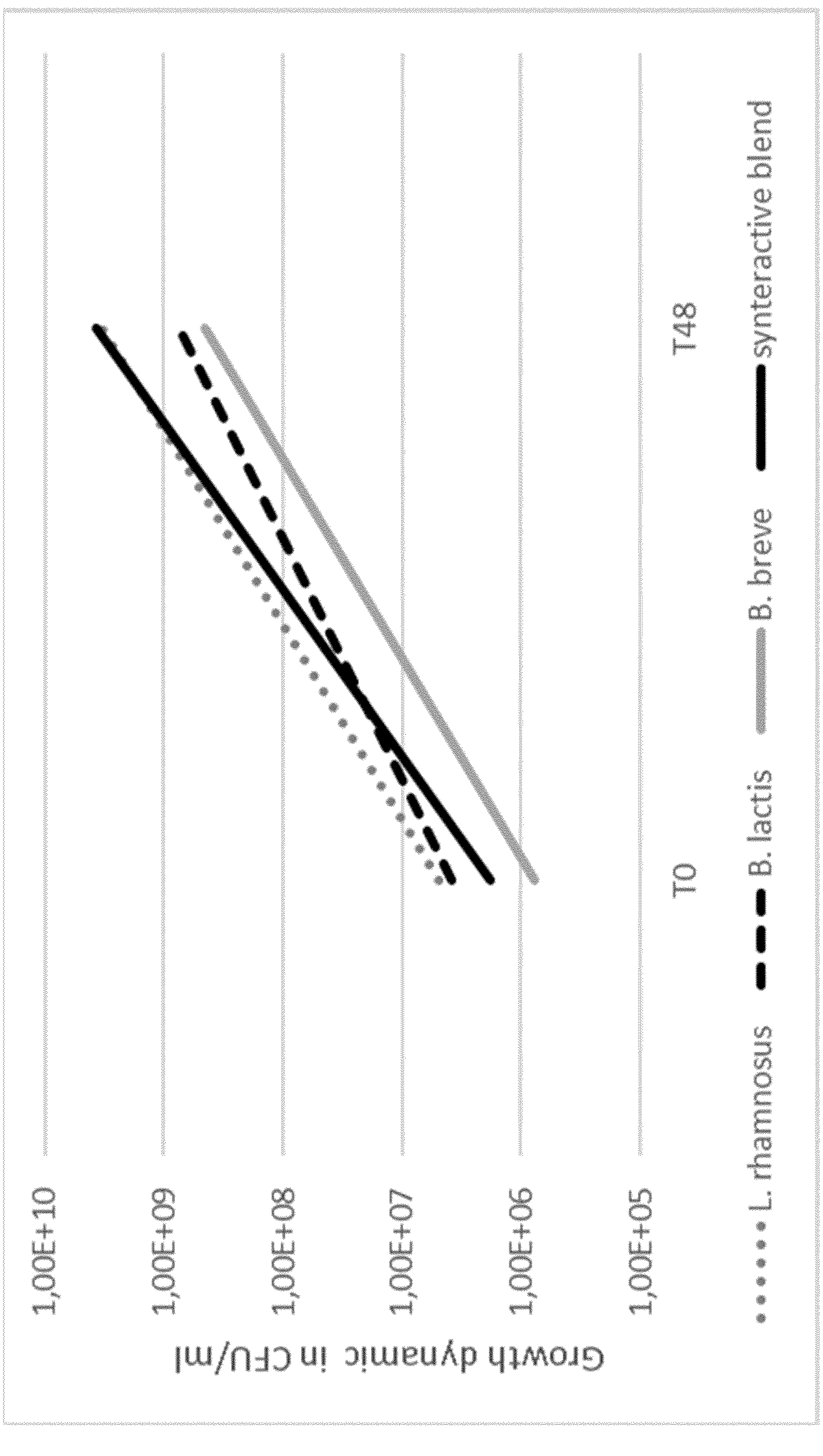
FIG. 1 is a graph comparing the growth performance of single probiotic strains and a synergistic blend.

Any strain of *Lactobacillus gasseri, Lactobacillus rhamnosus, Bifidobacterium breve* and *Bifidobacterium animalis* subsp. *lactis* may be used according to the invention, in any ratio. A ratio of 1:1:1 expressed as cell count is preferred. Combination of any strain of *Lactobacillus rhamnosus, Bifidobacterium breve* and *Bifidobacterium animalis* subsp. *lactis* is preferred when used for babies and infant till the completion of the weaning phase.

Combination of any strain of *Lactobacillus rhamnosus, Bifidobacterium breve* and *Lactobacillus gasseri* is preferred when used for weaned infants, pregnant women, lactating mothers and adults.

In addition to the new strains deposited at BCCM/LMG collection, other preferred strains, listed below, are freely available on the market and may be used according to the invention:

*Bifidobacterium breve* M16V at the BCCM/LMG collection at Ghent University (Belgium) as deposit number LMG 23729.

*Lactobacillus rhamnosus* HN001 at the Australian Government Analytical Laboratories (AGAL) as deposit number NM97/09514.

*Bifidobacterium animalis lactis* HN019 at the Australian Government Analytical Laboratories (AGAL) as deposit number NM97/09513.

A blend consisting of *Bifidobacterium breve* M16V, *Lactobacillus rhamnosus* HN001 and *Bifidobacterium animalis lactis* HN019 in 1:1:1 ratio (hereinafter blend A) is particularly useful as food supplement in babies till the weaning completion.

A blend consisting of *Lactobacillus gasseri* LMG P-30998, *Lactobacillus rhamnosus* LMG P-31000 and *Bifidobacterium breve* LMG P-30999 in 1:1:1 ratio (hereinafter blend B) is particularly useful as food supplement in post-weaning infants as well as in adults.

The probiotic blends of the invention revealed a higher capacity to interact with the mucosa of the host due to better performances of growth in different food matrices.

Probiotic food supplements of the invention can be administered in various forms, such as tablets, sticks, pills, oil drops, etc. containing at least 10^8 CFUs per gram or per ml.

The properties of the probiotic blends of the invention are disclosed in the following experimental section.

Probiotic Features (Resistance to Simulated Gastric Juice) of Synergistic Blends Versus Single Pure Probiotic Strains Simulated gastric fluid (SGF), mimicking assumption of probiotics in full stomach condition, was prepared by adding HCl to a solution of 2 g/l NaCl and adjusting the pH to either 1.2±0.1 or 3.4±0.1 to mimic high and low acidity conditions, respectively. The different pH values were chosen to represent different phases of the digestion process. The HCl/NaCl solution to a volume of 1 litre was added of sodium taurocholate (final concentration of 80 μM), lecithin (final concentration of 20 μM), 0.1 mg/ml pepsin. It has been reported that the consumption of probiotics during meals reduces the loss of vitality of probiotics. The results obtained for blends and pure single strains for full stomach at the 2 different pH as reported by Fredua-Agyeman et al are reported below. For all tested conditions 4 different time of analyses were set: T0, T15, T30, T60. At this time points viable decimal counts were performed; in the case of co-presence of lactobacilli and bifidobacteria two differential vital counts were performed, respectively on MRS agar and on TOS-mupirocin. MRS was incubated 48 h at 37° C. under anaerobic conditions, in order to assess only lactobacilli viable counts, instead TOS-MUP was incubated 72 h at 37° C. under anaerobic conditions.

Value 0 in the following tables means "below the detection limit" of the method, around 2 log 10 CFUs.

Full State Stomach—High Acidity pH 1,2

TABLE 1 growth (in log10 CFUs) at different timepoints (T0, T15, T30 and T60) of single pure strains and blends following exposure to SGF at pH 1.2.

| Strain/Blend | T0 | T15 | T30 | T60 |
|---|---|---|---|---|
| *L. rhamnosus* LMG P-31000 | 9.32 | 8.22 | 6.07 | 0.00 |
| *L. gasseri* LMG P-30998 | 8.32 | 8.78 | 8.42 | 7.65 |
| *Bif. breve* LMG P-30999 | 7.81 | 5.30 | 0.00 | 0.00 |
| *L. rhamnosus* HN001 | 9.21 | 8.27 | 6.37 | 0.00 |
| *B. lactis* HN019 | 8.17 | 7.87 | 6.16 | 2.74 |
| *B. breve* M16V | 8.63 | 8.44 | 6.01 | 4.02 |
| blend A | 8.04 | 7.80 | 0.00 | 0.00 |
| blend B | 9.08 | 7.84 | 4.56 | 0.00 |

Full State Stomach—Low Acidity pH 3,4

TABLE 2 growth (in log10 CFUs) at different timepoints (T0, T15, T30 and T60) of single pure strains and blends following exposure to SGF at pH 3.4.

| Strain/Blend | T0 | T15 | T30 | T60 |
|---|---|---|---|---|
| *L. rhamnosus* LMG P-31000 | 9.31 | 9.28 | 9.27 | 9.22 |
| *L. gasseri* LMG P-30998 | 8.32 | 8.78 | 8.42 | 8.10 |
| *Bif. breve* LMG P-30999 | 8.71 | 8.69 | 8.34 | 8.19 |
| *L. rhamnosus* HN001 | 9.31 | 9.26 | 9.26 | 9.20 |
| *B. lactis* HN019 | 8.68 | 8.55 | 8.21 | 8.12 |
| *B. breve* M16V | 8.78 | 8.61 | 8.31 | 8.15 |
| blend A | 8.98 | 8.99 | 8.91 | 8.83 |
| blend B | 9.13 | 9.07 | 9.07 | 9.02 |

Following in-vitro assays presented above, it is possible to conclude that when blends A and B are assumed in full stomach condition and specifically up to 30 min from the end of a meal, in correspondence with pH increase, the original ability of probiotic strains to survive gastric passage is maintained. In harsh conditions, like during the meal, with lower pH values, or in fasted stomach conditions, the viability of the blended strains is significantly affected.

Probiotic Features (Adhesiveness to Human Gut) of Synergistic Blend Versus Single Pure Probiotic Strains The capacity of to adhere to human gut following ingestion is one of the main features required to a beneficial strain to exert its probiotic activity. This trait is required to assure the persistence of the probiotic in the gut and therefore to confer its beneficial impact on human gastro-intestinal mucosa. Due to the requirement for non-invasive approach to the study of food supplements, in-vitro models based on cultured immortalized human cell lines are usually applied to the assessment of the adhesiveness of probiotics.

The assay was conducted in order to compare the adhesive ability expressed by single pure probiotic strains versus synergistic blend. Blending is in fact believed to be sometimes detrimental, due to antagonism phenomenon, to the global beneficial features of a multistrain product.

The adhesion was evaluated as the percentage of adhered bacteria to the human immortalized cell line HT29-MTX compared to the initial dose of the inoculum. The HT29-MTX mucus-producing cell line was routinely cultured in DMEM High Glucose (Dulbecco's Modified Eagle Medium)+10% decomplemented foetal calf serum, 50 μg/ml di L-glutamine at 37° C. with 5% di C02. Two days before the adhesion test, human cells were rinsed with a saline solution, treated with trypsin, counted and diluted at a concentration of $2.5\times10^5$ cells/ml. 1 ml of this solution was seeded in a 24-well plate. A total of 5 wells were seeded in order to perform the test, 3 for the single strain, one for the mix and one for the technical control of the analysis. The 24-well plate was incubated for 48 h at 37° C. with 5% di CO2 until cells reached the confluence. The day of the adhesion test, human cells were checked for the confluence, and obtained the positive response, the 5 wells were washed with the saline solution and incubated for 1 h with 875 mî of DMEM High Glucose (Dulbecco's Modified Eagle Medium)+1% decomplemented foetal calf serum at 37° C. with 5% CO2. An extra well without cells was inoculated with 875 mî of DMEM medium. This control-well act as a TO to precisely quantify the dose of microorganisms incubated with cells and to calculate the percentage of adhesion. 1 g of the three strains were diluted until the concentration of 1*10A7 cell/ml was reached. The mix suspension test solution was prepared by using respectively 1 ml of the three strains mixed in ratio 1:1:1. 125 mî of the probiotic suspensions prepared were used to inoculate the 5 wells seeded with the human cells line and the control well. The time of contact between cells and probiotic was of 60 minutes at 37° C. with 5% of CO2. The Multiplicity Of Infection (MOI) between bacteria and cell line was 5:1. After the incubation time, the sample in the control well was harvested and serially diluted and plated, for the other wells the medium was removed and the cell monolayer was washed three times with 1 ml of saline solution for 5 minutes. The cell monolayers with adhered probiotic bacteria were inoculated with 100 mî of trypsin and incubated for 5 minutes at 37° C. to break the cell bonds and the solution was recovered with 900 mî of MRD (Maximum recovery diluent, Difco, BD). The sample was serially diluted and plated to quantify the adhesive ability of single probiotic strains as well as that of synergistic blend. Table 3 summarises adhesion percentages for all the tested conditions.

TABLE 3 adhesion % of single strains, synergistic blends A and B and generic blends A and B to human cultured gut cell line

| Strain/Blend | Adhesion (%) |
|---|---|
| *L. rhamnosus* ATCC 53013 | 74 |
| *L. rhamnosus* LMG P-31000 | 69 |
| *L. gasseri* LMG P-30998 | 66 |
| *Bif. breve* LMG P-30999 | 64 |
| *L. rhamnosus* HN001 | 62 |
| *B. lactis* HN019 | 73 |
| *B. breve* M16V | 65 |
| synergistic blend A | 73 |
| synergistic blend B | 84 |
| generic blend A | 70 |
| generic blend B | 60 |

The results confirm the absence of antagonism inside blend A, since total adhesion percentage demonstrates that more than 70% of the total population of viable cells of blend A adheres to human gut cell line. Moreover, the results support the observation that blend A supports the increase in the total % of adhesion compared to single *Bifidobacterium* spp. and *L. rhamnosus* strains. Blend B showed synergism between combined probiotic strains, showing a % of adhesion significantly higher than those shown by single pure strains. In fact, the 3 strains composing blend B showed an average adhesion to gut cell line in culture of 66%.

Probiotic Features (Pathogen Displacement) of Synergistic Blend Versus Single Pure Probiotic Strains Many scientific evidences are available about the ability of probiotics to displace pathogens both in-vitro and in-vivo. Entity of competition, leading to displacement, depends on dose as well as on the protocol of treatment. The assay was conducted based on a modification of Coman et al. (2015). The assay is based on an in-vitro model that use the eukaryotic immortalized human colon-derived cell line HT29. The displacement assay consists of two subsequent steps; the first phase is represented by the infection between the pathogen and the human cell line during 1-hour incubation. This phase is followed by two washing rounds to remove unbonded bacteria. The second phase consist of the incubation of the probiotic with the cells previously infected for 1-hour followed by a washing step and the recovery of the pathogen bacteria still bound to human cells. The assay was conducted with the blends of the invention as well as with pure probiotic strains, involving pathogen *Salmonella enterica serovar enterica* Poona NCTC 4840. Table 4 reports the adhesion percentages of the pathogens in the presence of probiotics. The "undisturbed" adhesion of pathogens alone is considered as 100%.

TABLE 4

Salmonella adhesion (%) to HT29-MTX mucus-producing cell line following probiotic intervention

| Strain/Blend | Salmonella adhesion % |
|---|---|
| Negative control | 100 |
| *L. rhamnosus* LMG P-31000 | 87.8 ± 1.0 |
| *L. gasseri* LMG P-30998 | 0.0 |
| *Bif. breve* LMG P-30999 | 87.8 ± 0.9 |
| *L. rhamnosus* HN001 | 91.4 ± 0.8 |
| *B. lactis* HN019 | 91.5 ± 1.0 |
| *B. breve* M16V | 95.2 ± 0.8 |
| synergistic blend A | 89.2 ± 0.8 |
| synergistic blend B | 78.3 ± 0.9 |

The results presented above show that the adhesion of *Salmonella enterica* to in-vitro HT29-MTX mucus-producing gut cells is disturbed to a different extent depending on the probiotic strain. Blend A reduced adhesion of Salmonella of almost 11% in 1 hour while pure single strains resulted less efficient (from 5 to 9%). Blend B reduced the adhesion of *Salmonella* to HT29-MTX cells of about 22%. Single strains were less efficient with % of adhesion reduction of 12-13% but notably *L. gasseri* LMG P-30998 was able to totally antagonize *Salmonella* when tested as pure strain.

Mucus-producing cell line is considered as the most representative model of human gut mucosa, due to the presence of the mucus layer on its surface, mimicking human mucosa. Nevertheless, the presence of mucus layer seems to affect the repeatability and reproducibility of the results obtained for in-vitro adhesion assays. In order to achieve more reliable results, the above-mentioned tests were repeated in the same conditions by using HT-29 cell line instead of HT29-MTX.

TABLE 5

*Salmonella* adhesion (%) to HT-29 gut cell line following probiotic intervention

| Strain/Blend | *Salmonella* adhesion % |
|---|---|
| Negative control | 100 |
| *L. rhamnosus* LMG P-31000 | 73.2 ± 0.2 |
| *L. gasseri* LMG P-30998 | 54.9 ± 0.5 |
| *Bif. breve* LMG P-30999 | 62.8 ± 0.3 |
| *L. rhamnosus* HN001 | 71.4 ± 0.2 |
| *B. lactis* HN019 | 68.2 ± 0.4 |
| *B. breve* M16V | 73.9 ± 0.1 |
| blend A | 68.1 ± 0.5 |
| blend B | 60.2 ± 0.4 |

The results presented in Table 5 show that the adhesion of *Salmonella enterica* to in-vitro HT-29 gut cells is disturbed to a different extent depending on the probiotic strain. Blend A was able to reduce adhesion of *Salmonella* of almost 32% in 1 hour while 2 out of 3 pure single strains resulted less efficient (from 26 to 29% reduction). Blend B reduced the adhesion of *Salmonella* to HT29-MTX cells of about 40%. In this case the blend seems to take great advanced from the presence of *L. gasseri* LMG P-30998 that was confirmed as the most efficient strain in antagonising Salmonella in adhesion to HT-29 cells.

Growth in Laboratory Culturing Medium of Synergistic Blend Versus Single Pure Probiotic Strains The objective of this assay was to assess the putative antagonism between strains which represents the main challenge, negatively affecting probiotics viability, that multistrain probiotic products have to face. Antagonism finally results in a reduction in viability of probiotics upon ingestion and gut transit by consumers. This relevant issue is often neglected but there are very well documented risks of antagonism between strain belonging to close phylogenetical groups.

The three strains were assessed for their growth abilities as pure strains or in multistrain combination (blend) in ratio 1:1:1. Laboratory medium De Man, Rogosa & Sharpe was incubated during 48 h under anaerobic condition at 37° C. Viable counts were performed at the T0 and at T48. The growth of synergistic blends in 48 hours compared with growth performance of single strains FIG. 1.

The figure shows that growth of strains blended inside synergistic blend was not affected by blending since the growth performances achieved following 48-hours incubation, are totally comparable to growth of single strains. Therefore, no antagonism was taking place in synergistic blends.

Growth in Foods of Synergistic Blend Versus Single Pure Probiotic Strains

Growth in Formula Milk (Stages 1, 2 and 3), from 0 to More than 3-Years-Old Infants Several different samples of commercial formula milk for formula-fed babies were retrieved form the market. Products were referred to the 4 stages of baby's growth, means stage-1 for babies from birth to 6 months of age, stage-2 from 6 to 12 months, stage-3 for toddlers from 1 to 3 years and stage-4 for infants older than 3 years of age. The ability of blends A and B to grow into these different types of formula milk was checked in comparison with single pure strains, in order to assess potential synergistic interaction between blends and food substrate. The capacity to use formula milk as nutritional substrate by probiotics was assessed by calculating the difference between T0 and the T post-incubation concentration in viable bacterial cells. The difference was then converted in log 10 CFUs in order to compare the results.

TABLE 6 growth increase in log10 CFUs for the tested strains/blends in different formula milks stage-1

| Strain/Blend | Aptamil | Humana | Mellin | Nidina | Plasmon | Ofmom (Korea) | Ofmom (China) |
|---|---|---|---|---|---|---|---|
| *L. rhamnosus* LMG P-31000 | 2.89 | 2.88 | 2.89 | 2.45 | 2.90 | 2.66 | 2.68 |
| *L. gasseri* LMG P-30998 | 0.86 | 1.15 | 0.66 | 1.94 | 2.30 | 1.43 | 1.18 |
| *Bif. breve* LMG P-30999 | 0.00 | 0.00 | 0.00 | 0.00 | 2.45 | 1.41 | 1.61 |
| *L. rhamnosus* HN001 | 2.08 | 2.30 | 2.53 | 2.18 | 0.00 | 2.46 | 2.38 |
| *B. lactis* HN019 | 0.43 | 0.66 | 0.26 | 1.36 | 2.74 | 1.04 | 1.15 |
| *B. breve* M16V | 0.43 | 0.26 | 0.26 | 0.56 | 2.41 | 1.67 | 1.88 |
| blend A | 2.88 | 2.97 | 2.95 | 2.93 | 2.65 | 2.91 | 2.80 |
| blend B | 3.04 | 2.96 | 2.88 | 2.80 | 3.20 | 2.83 | 2.88 |

TABLE 7

| growth increase in log10 CFUs for the tested strains/blends in different formula milks stage-2 | | | | | | | |
|---|---|---|---|---|---|---|---|
| Strain/Blend | Aptamil ® | Humana ® | Mellin ® | Nidina ® | Plasmon ® | Ofmom (Korea) ® | Ofmom (China) ® |
| *L. rhamnosus* LMG P-31000 | 2.78 | 2.72 | 1.96 | 2.40 | 3.15 | 2.72 | 2.72 |
| *L. gasseri* LMG P-30998 | 1.04 | 0.81 | 1.20 | 1.04 | 1.81 | 1.23 | 1.20 |
| *Bif. breve* LMG P-30999 | 0.00 | 0.00 | 0.00 | 0.00 | 0.00 | 1.45 | 1.66 |
| *L. rhamnosus* HN001 | 2.08 | 2.23 | 2.08 | 2.18 | 2.40 | 2.52 | 2.56 |
| *B. lactis* HN019 | 1.91 | 1.15 | 1.51 | 1.96 | 2.61 | 1.91 | 1.74 |
| *B. breve* M16V | 1.54 | −0.04 | 0.66 | 1.45 | 0.56 | 2.11 | 1.79 |
| blend A | 2.79 | 2.95 | 2.67 | 3.04 | 2.11 | 2.95 | 3.15 |
| blend B | 2.74 | 2.84 | 2.36 | 2.57 | 3.04 | 2.85 | 2.99 |

TABLE 8

| growth increase in log10 CFUs for the tested strains/blends in different formula milks stage-3 | | | | | | | | | |
|---|---|---|---|---|---|---|---|---|---|
| Strain/Blend | Aptamil | Coop | Granarolo | Humana | Mellin | MIO | Plasmon | Ofmom (Korea) | Ofmom (China) |
| *L. rhamnosus* LMG P-31000 | 2.08 | 2.46 | 2.66 | 2.18 | 1.67 | 2.74 | 2.89 | 2.84 | 2.83 |
| *L. gasseri* LMG P-30998 | 1.15 | 1.40 | 1.08 | 0.91 | 1.18 | 1.66 | 2.20 | 1.36 | 1.30 |
| *Bif. breve* LMG P-30999 | 0.00 | 0.00 | 0.00 | 1.52 | 0.00 | 0.00 | 0.56 | 1.72 | 0.74 |
| *L. rhamnosus* HN001 | 1.72 | 2.20 | 2.08 | 2.32 | 1.75 | 2.20 | 2.53 | 2.48 | 2.53 |
| *B. lactis* HN019 | 1.00 | 0.66 | 0.74 | 1.55 | 0.26 | 0.66 | 1.43 | 1.11 | 1.38 |
| *B. breve* M16V | 0.86 | 0.26 | −0.04 | 0.43 | 0.96 | 0.26 | 0.00 | 0.81 | 2.26 |
| blend A | 2.80 | 3.08 | 2.88 | 2.76 | 2.74 | 3.32 | 2.99 | 3.11 | 3.26 |
| blend B | 2.28 | 2.75 | 2.79 | 2.23 | 2.45 | 2.83 | 3.08 | 3.08 | 3.04 |

TABLE 9

| growth increase in log10 CFUs for the tested strains/blends in different formula milks stage-4 | | | |
|---|---|---|---|
| Strain/Blend | Aptamil ® | Mellin ® | Plasmon ® |
| L. rhamnosus LMG P-31000 | 2.18 | 2.04 | 3.28 |
| *L. gasseri* LMG P-30998 | 1.04 | 0.96 | 2.45 |
| *Bif. breve* LMG P-30999 | 0.00 | 0.00 | 0.26 |
| *L. rhamnosus* HN001 | 1.86 | 1.91 | 2.36 |
| *B. lactis* HN019 | 0.26 | 0.91 | 1.85 |
| *B. breve* M16V | 0.43 | 0.56 | 0.43 |
| blend A | 2.15 | 2.15 | 2.96 |
| blend B | 2.71 | 2.60 | 3.26 |

Considering overall data on growth of probiotic single strains and synergistic blends in formula milk, it is possible to observe that blends present higher growth increase. The development of probiotics in formula milk results to be largely improved by blending, which appears to significantly exploit the synergy between beneficial bacteria and the food matrix in which it is driven to consumers.

Different commercial brands were considered. Basically, some of them were found to better support probiotics' growth, probably due to the higher content in oligosaccharides as well as the presence of a functional ingredient (Plasmon brand) able to promote bifidobacteria.

Stage 1 formula milk: bifidobacteria and *L. gasseri* were found to present poor growth on some brands, like Aptamil®, Humana®, Melling and Nidina®, while *L. rhamnosus* presented significant ability to grow on these types of formula milk stage 1. Other brands, like Plasmon® and Ofmom®, supported better the growth of bifidobacteria and *L. gasseri* but anyway less than *L. rhamnosus*. Blends A and B were confirmed to grow better than single strains on all of the tested brands.

Stage 2 formula milk: bifidobacteria and *L. gasseri* were found to present poor growth on some brands, like Aptamil®, Humana®, Melling, Nidina® and Plasmon®, while *L. rhamnosus* presented significant ability to grow on these types of formula milk stage 2. Brand Ofmom® supported better the growth of bifidobacteria and *L. gasseri* but anyway less than *L. rhamnosus*. Blends A and B were confirmed to grow better than single strains on all of the tested brands.

Stage 3 formula milk: bifidobacteria and *L. gasseri* were found to present poor growth on some brands, like Aptamil®, Humana®, Mellin®, Nidina® and Plasmon®, while *L. rhamnosus* presented significant ability to grow on these types of formula milk stage 3. Brand Ofmom® supported slightly better the growth of bifidobacteria and *L. gasseri* but anyway less than *L. rhamnosus*. Blend A and particularly blend B were confirmed to grow better than single strains on all of the tested brands.

Stage 4 formula milk: bifidobacteria and *L. gasseri* were found to present poor growth on some brands, like Aptamil® and Mellin®, while *L. rhamnosus* presented significant ability to grow on these types of formula milk stage 4. Brand Plasmon supported slightly better the growth of bifidobacteria and *L. gasseri* but anyway less than *L. rhamnosus*. Blend A and particularly blend B were confirmed to grow better than single strains on all of the tested brands.

The blends of the invention have been observed to be able to interact with the baby food to a large extent, generating in most of the cases about 3 log 10 CFUs growth increase.

Performances shown by pure single probiotic strains are in the majority of the tested cases lower than synergistic blends. Some strains, with special reference to bifidobacteria, were in fact completely unable to ferment the substrate since they were confirmed to require the concomitant presence of lactobacilli inside synergistic blends, to metabolize formula milk.

CONCLUSIONS

Despite the fact that commercial trends seem to drive towards complex multistrain probiotic formulations, very poor scientific evidences are available. Very often, due to ecological reasons, strains belonging to the phylogenetically related species present strong antagonism through the production and release, for instance, of antimicrobial metabolites like bacteriocins, hydrogen peroxide, toxins, etc. These substances allow a single strain to defend itself and its substrates towards the presence of other bacteria, generating a competitive relationship. This mechanism represents the basis for the eubiotic equilibrium typical of the stable ecological niches. But when this antagonism takes place inside a commercial mixture of probiotic strains, it negatively affects the viability of probiotics, which is essential for their beneficial action on the consumer. It is therefore very important to carefully select probiotic strain and elaborate mix of probiotics in which the antagonism phenomena are absent and, conversely, synergy between components is promoted in order to assures better beneficial effects for the consumer.

The blends of the invention have been designed in order to achieve the deletion of any antagonistic relationship and to maximise the beneficial activity thanks to the synergy between the components. The synergistic interaction between the 3 strains included in the blends has been measured by evaluating some very relevant probiotic features, like the survival to the simulated gastric transit, the ability to adhere to simulated gut mucosa as well the capacity to antagonise gut pathogens (e.g. *Salmonella*). These very relevant characteristics of probiotics resulted to be significantly improved when probiotics were included in the synergistic blends instead that considered alone as single probiotic strains. These results clearly indicated that strains in the blends of the invention were not antagonizing each other but they were collaborating in exerting better beneficial actions.

Moreover, the blends were tested in milk formulas, as representative of food essential in the first phases of human life as well as before and after weaning. Four different types of formula milk, from stage-1 to stage-4, of several commercial brands were tested for the ability to support the growth of synergistic blends versus single pure probiotic strains. Synergistic blends were confirmed to have a strong synergy with food, as indicated by the significant overall growth level achieved by blends compared to single probiotic strains. Pure bifidobacteria and *L. gasseri* were demonstrated to be unable to grow in most of the formula milks considered, unless those products containing high amounts of added oligosaccharides. Even in these cases the growth of these species was lower that *L. rhamnosus*. But when bifidobacterial and/or *L. gasseri* were mixed with *L. rhamnosus* in the blends A or B their synergy assured the ability of all of the components to perform better in milk.

Probiotic Features (Ability to Stimulate the Release of Glucagon) of Synergistic Blends Versus Single Pure Probiotic Strains The ability of the blends to stimulate the release of glucagon (GLP-1) by a cultured human cell line (NCI-H716) derived from colorectal cancer blends in comparison with the single strains and/or the positive control (chemical PMA) has been studied. Glucagon-like-peptide-1 (GLP-1) is a hormone released by the mucous membrane of the small intestine and colon in response to food ingestion. This hormone is of fundamental importance for stimulating the release of insulin, regulating gastric emptying and promoting the sense of satiety. This model provides evidence of the diabetogenic potential of certain foods.

Bacterial strains were tested for their ability, alone or in combination (blend), to stimulate the release of GLP-1 by the human cell line, in the presence of skim milk. The strains were tested (TEST A) in viable form, but also by means of their post-biotics (TEST B). Post-biotics are supernatants obtained from the liquid cultures of each strain and contain their bioactive metabolites. The results are reported in FIG. 2

Strains and Conditions Used (Figure Legends):

C−=negative control (human cells not treated, basal conditions); C+=positive control (phorbol myristate acetate PMA which induces an overproduction of GLP); 1 C+ skim milk=treatment of human cells with 0.5% skimmed milk,

*Bifidobacterium breve* M16V (invention); *Bifidobacterium breve* 2TA (LMG P-30999) (invention); *Bifidobacterium breve* ATCC 15700 (strain from the international collection ATCC); *Bifidobacterium breve* Bb03 (commercial strain); *Bifidobacterium lactis* HN019 (invention); *Bifidobacterium lactis* Bb12 (commercial strain); *L. gasseri* L6 (LMG P-30998) (invention); *L. rhamnosus* L13b (LMG P-31000) (invention); *L. rhamnosus* HN001 (invention); *L. rhamnosus* GG (commercial strain); *L. rhamnosus* SPO1 (commercial strain); Blend A (mix of strains *B. breve* M16V+*L. rhamnosus* HN001+*B. lactis* HN019); Blend B (mix of strains *L. gasseri* L6+*L. rhamnosus* L13b+*B. breve* 2TA). Blend A commercial is a commercial product (Ofmom Synteract Bimbi®) comprising Blend B.

Blend commercial (mix of strains *L. rhamnosus* GG+*B. lactis* Bb12+*B. breve* ATCC 15700).

The test results confirm that:

a) the blend works better than other commercial strains (in the form of viable strain and in the form of active metabolites), inducing glucagon levels at least similar than those of the positive controls;
b) the blend positively affects a marker indicative of the antidiabetic effect of foods;
c) the blend interacts better with the food matrix than the single components and the commercial strains.

Test A

Figure 2:
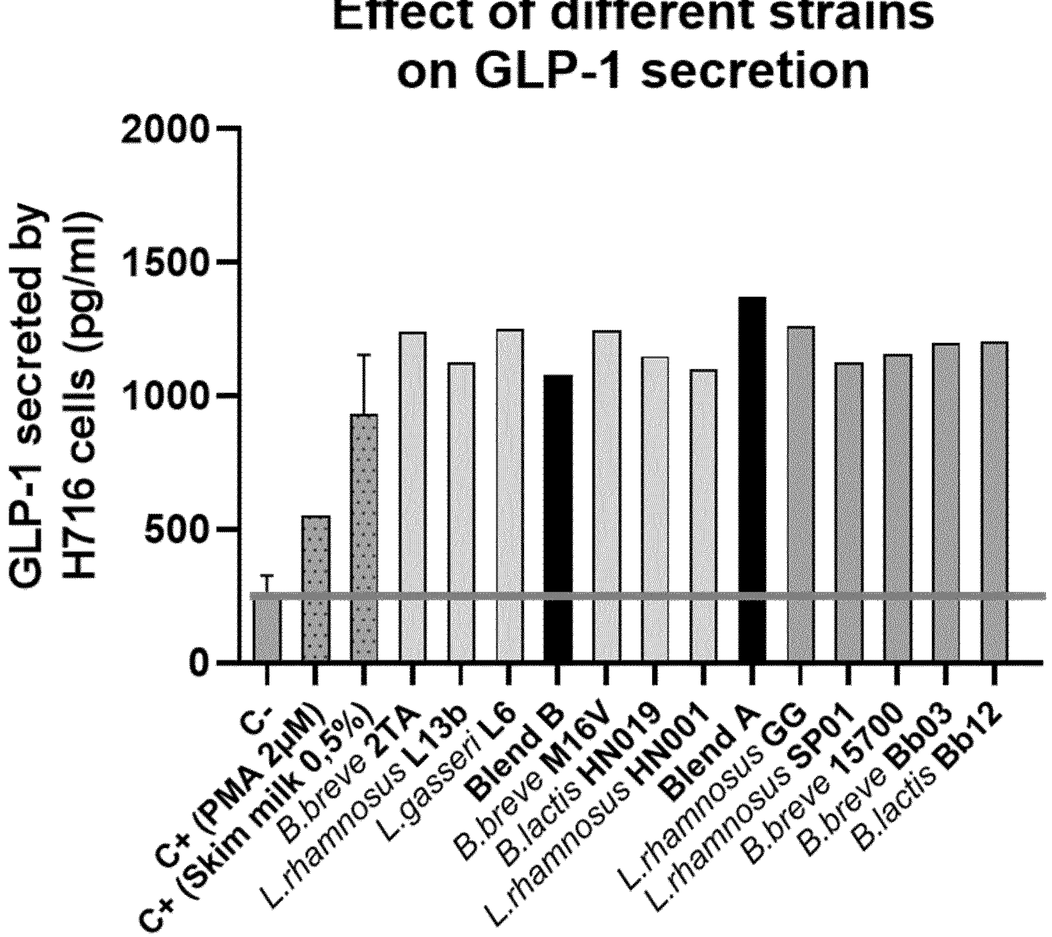
FIG. 2 is a graph showing the effect of different probiotic strains and blends on cultured cells.

The strains were tested in viable form. the results, reported in FIG. 2 show how the positive controls (PMA) induces an increase in GLP-1 secretion equal to approx. 500 pg/ml and skim milk a two-fold increase in the secretion. When viable strains interact with skimmed milk, a synergistic (synteractive) behaviour is induced and produced an increase in glucagon secretion, especially for Blend A which generates a secretion of approx. 1400 pg/ml. The commercial strains tested, while inducing a significant increase compared to skimmed milk, do not reach an effect comparable to that of Blend A.

Test B

Figure 3:
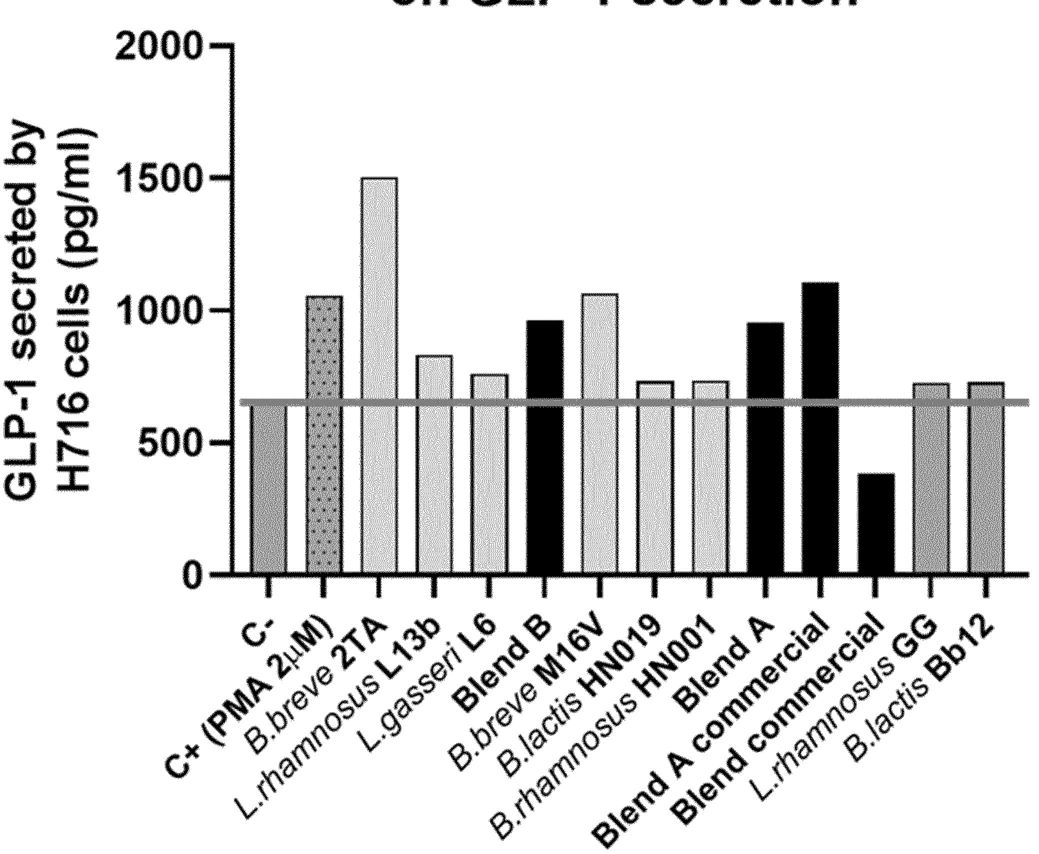
FIG. 3 is a graph showing the effect of metabolites of different probiotic strains and blends on cultured cells.

The bioactive metabolites contained in supernatants of the strains have been isolated; the strains were firstly grown in a suitable culture broth and, after growing, the cells were removed by centrifugation and resuspended with fresh culture medium, followed by incubation at 4° C. for 24 hours. Following a further centrifugation step, the cells were removed and the supernatants were subjected to the test. FIG. 3 shows that the positive control PMA induced an increase in glucagon level when compared to the negative control. Blend A and Blend B determine an induction effect of glucagon almost comparable to that of the positive control, even slightly higher in the case of the commercial formulation of Blend A (1200 pg/ml compared to 1000 for PMA). Blend A and Blend B induce the release of a significantly higher amount of glucagon when compared to commercial strains (GG, Bb12 and commercial blend).

REFERENCES

Deepika, G., Karunakaran, E., Hurley, C. R., Biggs, C. A. & Charalampopoulos, D. Influence of fermentation conditions on the surface properties and adhesion of *Lactobacillus rhamnosus* GG. Microb. Cell Fact. (2012). doi: 10.1186/1475-2859-11-116.

Dekker, J. W., Wickens, K., Black, P. N., Stanley, T. V, Mitchell, E. A., Fitzharris, P., Tannock, G. W., Purdie, G. and J. Crane (2009). Safety aspects of probiotic bacterial strains *Lactobacillus rhamnosus* HN001 and *Bifidobacterium animalis* subsp. *lactis* HN019 in human infants aged 0-2 years. International Dairy Journal 19, 149-154.

Duary, R. K., Rajput, Y. S., Batish, V. K. & Grover, S. Assessing the adhesion of putative indigenous probiotic lactobacilli to human colonic epithelial cells. Indian J. Med. Res. (2011). doi:10.4103/0971-5916.90992.

El-Abasy, A. E., Abou-Gharbia, A., H., Mousa, H. M. & Youssef, M. M. Mixes of Carrot Juice and Some Fermented Dairy Products: Potentiality as Novel Functional Beverages. Food Nutr. Sci. (2012). doi:10.4236/fns.2012.32034.

Johansson, M. L. et al. Administration of different *Lactobacillus* strains in fermented oatmeal soup: In vivo colonization of human intestinal mucosa and effect on the indigenous flora. Appl. Environ. Microbiol. 59, 15-20 (1993).

Joint FAO/WHO Working Group Report on Drafting Guidelines for the Evaluation of Probiotics in Food London, Ontario, Canada, April 30 and May 1, 2002.

Marshall E. & Mejia D. (2012) Traditional fermented food and beverages FAO Diversification booklet n. 21.

Tamang J P, Watanabe K, Holzapfel W H. Review: Diversity of Microorganisms in Global Fermented Foods and Beverages. Front Microbiol. 2016; 7:377. Published 2016 Mar. 24. doi:10.3389/fmicb.2016.00377.

Zhou, J. S., & Gill, H. S. (2005b). Immunostimulatory probiotic *Lactobacillus rhamnosus* HN001 and *Bifidobacterium lactis* HN019 do not induce pathological inflammation in mouse model of experimental auto-immune thyroidites. International Journal of Food Microbiology; 103:97-104.

Zhou, J. S., Gopal, P. K., Prasad, J.,& Gill, H. S. (2000). Potential probiotic lactic acid bacteria *Lactobacillus rhamnosus* (HN001), *Lactobacillus acidophilus*(HN017) and *Bifidobacterium lactis* (HN019) do not degrade gastric mucin in vitro. International Journal of Food Microbiology; 63:81-90.

Zhou, J. S., Rutherfurd, K. J., & Gill, H. S. (2005a). Inability of probiotic bacterial strains *Lactobacillus rhamnosus* HN001 and *Bifidobacterium lactis* HN019 to induce human platelet aggregation in vitro. Journal of Food Protection 68 (11); 2459-2464.

The invention claimed is:

1. A probiotic food supplement comprising:

a probiotic blend consisting of *Bifidobacterium breve* deposited as LMG 23729, *Lactobacillus rhamnosus* deposited as NM97/09514, and *Bifidobacterium animalis lactis* deposited as NM97/09513, wherein a cell count ratio of three strains is 1:1:1, wherein the probiotic blend exhibits an increased ability to stimulate glucagon release when co-administered with skim milk relative to respective single-strain controls under identical test conditions.

2. The probiotic food supplement according to claim 1, in form of solutions, sticks, powders, granulates, tablets, or capsules.

3. A probiotic food supplement comprising:

a probiotic blend consisting of *Lactobacillus* gasseri LMG P-30998, *Lactobacillus rhamnosus* LMG P-31000 and *Bifidobacterium breve* LMG P-30999, wherein a cell count ratio of three strains is 1:1:1.

* * * * *